United States Patent [19]

Stockwell

[11] Patent Number: 5,012,812
[45] Date of Patent: May 7, 1991

[54] APPLANATION TONOMETERS

[75] Inventor: Henry J. Stockwell, Roydon, England

[73] Assignee: Clement Clarke International Limited, Harlow, England

[21] Appl. No.: 633,685

[22] Filed: Jul. 25, 1984

Related U.S. Application Data

[63] Continuation of Ser. No. 333,682, Dec. 23, 1981, abandoned.

[51] Int. Cl.⁵ .................................................. A61B 3/16
[52] U.S. Cl. ...................................... 128/652; 128/651
[58] Field of Search ................. 128/645, 646, 651, 652

[56] References Cited

U.S. PATENT DOCUMENTS 3,952,585 4/1976 Perkins et al. ...................... 128/652

Primary Examiner—Randall L. Green
Assistant Examiner—K. Reichle
Attorney, Agent, or Firm—Wenderoth, Lind & Ponack

[57] ABSTRACT

An applanation tonometer having an applanating member mounted on an arm pivoted in a body; a manual adjustment knob mounted in the body; and two spiral springs in series between the knob and the arm via an intermediate spindle, thus giving a low-rate spring arrangement without the attendant difficulty of the spring coils binding on each other.

3 Claims, 3 Drawing Sheets

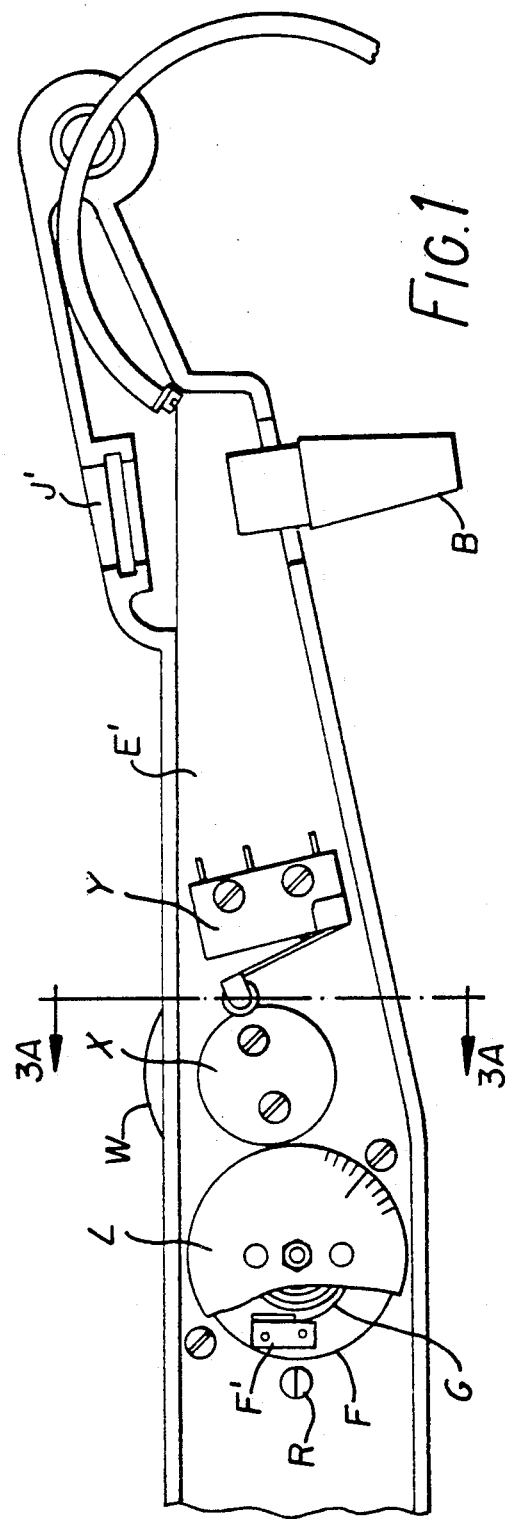
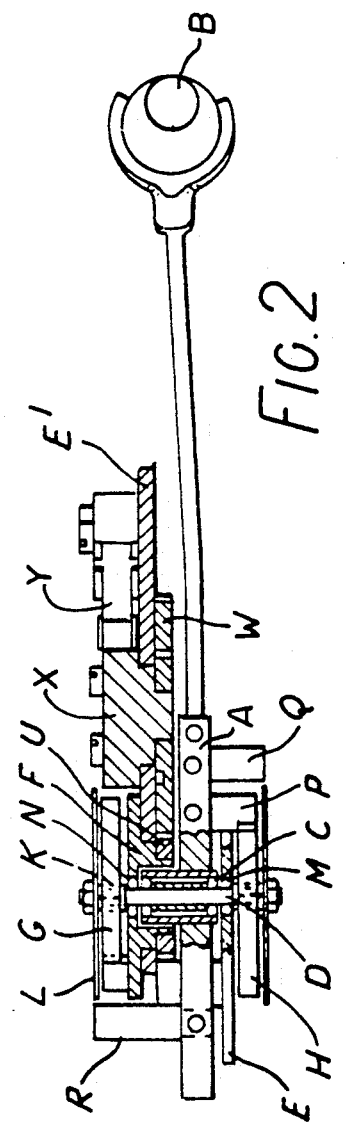

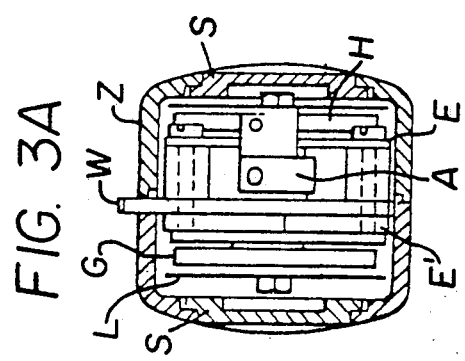
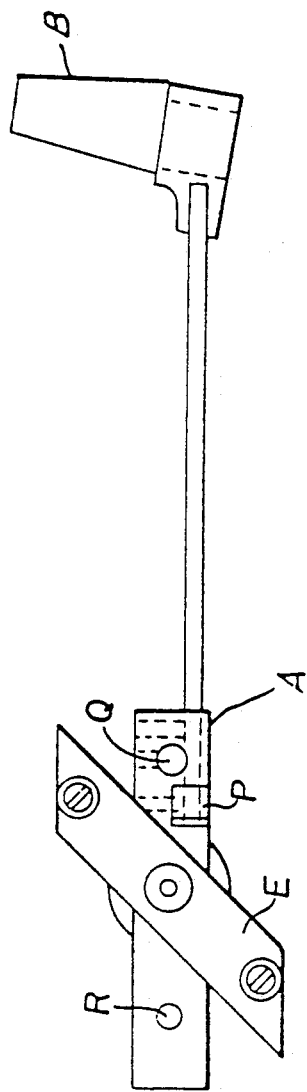
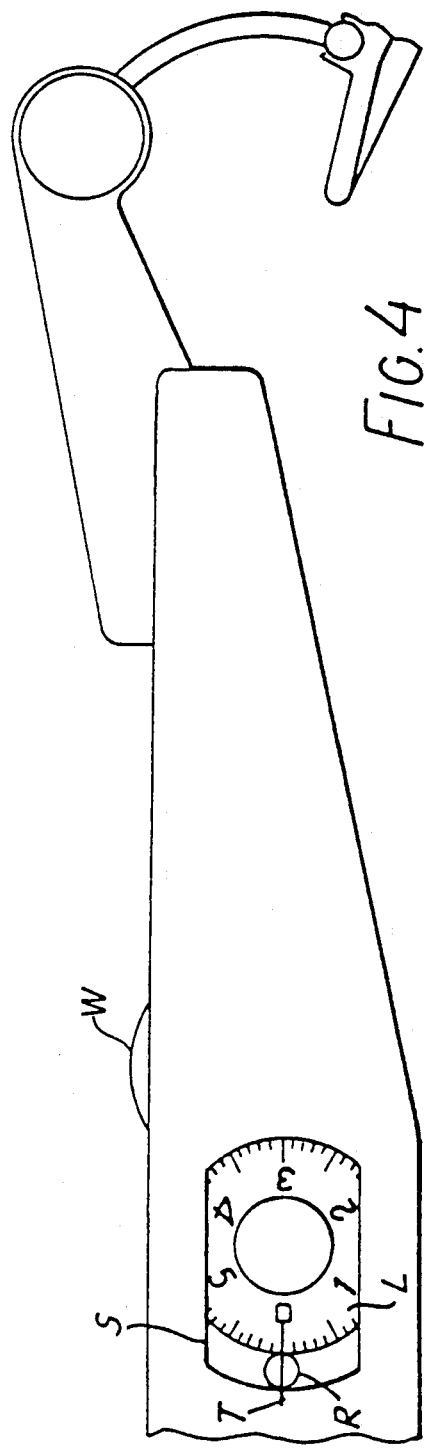

APPLANATION TONOMETERS

This application is a continuation of now abandoned application Ser. No. 333,682, filed Dec. 23, 1981.

In certain eye diseases, notably glaucoma, it is desirable to measure the intraocular pressure; instruments for doing this are called tonometers. The art is well known, and instruments based on several different principles have been proposed.

The present invention is an improvement on a previous design type, namely applanation tonometers, whose features are set out in U.S. Pat. No. 3,952,585 in the names of Edward Sylvester Perkins and H. J. Stockwell.

In U.S. Pat. No. 3,952,585 there is described an arrangement in which an applanating member is carried on an arm which is coupled to a manual adjustment knob via a spiral spring. The knob is calibrated to derive the spring tension when the applanating member applies the required pressure to the eye.

The main disadvantage of this design is that the scale reading is correct in only one rotary position of the pivot member, due to the fact that rotary displacement of the applanating member either winds up or unwinds the spring. Therefore, there may be a small error in estimating the force actually used at the moment when the pressure is determined, due to the position of the applanation member at that time, compared with its position when calibrated.

An obJect of the present invention is to reduce that error.

According to the invention there is provided an applanating tonometer having a body; an applanating member mounted on an arm; a spindle pivoted in the body, the arm being rotatably mounted on the spindle; two spiral springs; and a manual adjustment knob rotatable with respect to the body, the first spring being coupled at one end to the knob and at the other end to the spindle and the second spiral spring being coupled at one end to the spindle and at the other end to the arm. This arrangement provides that the springs are in series between the knob and the arm, thus providing a low-rate spring arrangement without the attendant difficulty of the spring coils of the single spring of the prior art device binding on each other.

The knob may be calibrated to give the tonometer reading. However, in a preferred embodiment of the invention a graduated scale is provided on the spindle so that the position of the arm can be read with respect to the spindle. Furthermore, a fiduciary mark is made on the body to allow the arm to be aligned therewith to a calibrating position. This arrangement allows accurate measurement of the spring tension at the arm calibrating position and provides compensation for errors induced by reading the spring tension where the arm is not properly positioned.

The invention will further be described with reference to the accompanying drawings, in which:

FIG. 1 is a side elevation of the mechanism of an applanation tonometer according to the invention with the near side half of the body removed;

FIG. 2 is a partially cross-sectional from beneath the mechanism of FIG. 1 with body omitted;

FIG. 3 is an elevation of the mechanism from the other side; with the body omitted for clarity FIG. 3A is a section on line 3A—3A of FIG. 1 with some parts omitted for clarity;

FIG. 4 is an elevation of the tonometer from the first side; and

Figure 5:
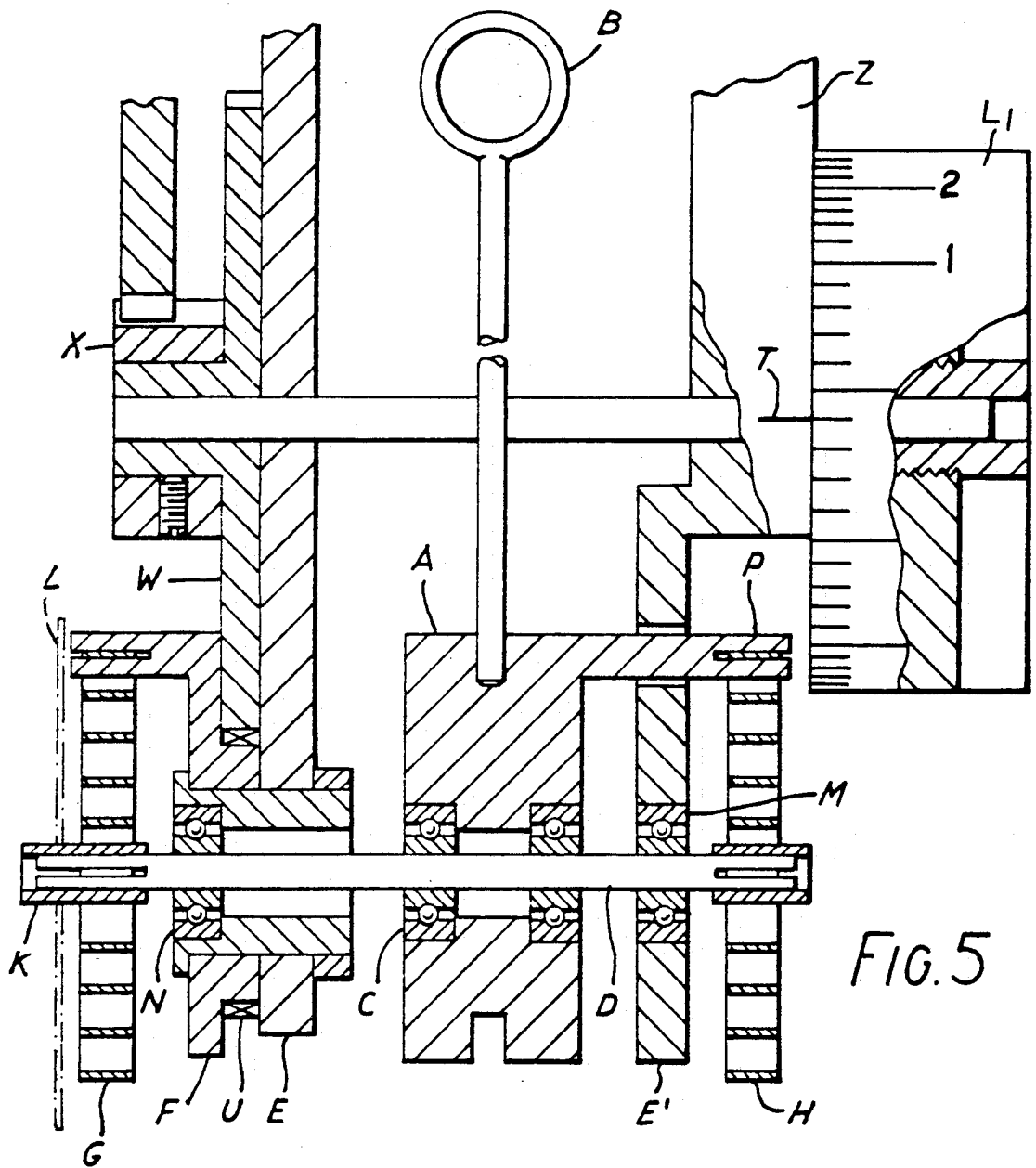
FIG. 5 is a partial cross-sectional view of another embodiment of the invention.

Referring to the drawings, an arm A carrying an applanating member B is rotatably mounted on low friction bearings C about a rotatably mounted spindle D which is itself mounted in low friction bearings, one of which, M, is supported on a support frame E mounted in the body Z of the tonometer in a conventional manner and the other, N, in an anchor wheel F. Inspection eyepiece J' is carried on the body Z opposite the applanating member B in the conventional manner.

The spindle D has a slot at each end to accomodate springs G and H. The springs are mounted in series so that for an upward movement (into the body) of applanating member B in FIG. 1, and a consequent counterclockwise movement of arm A and spindle D, both springs are wound up. The direction of winding of spring G in FIG. 1 is shown. The direction of winding of spring H is the same. The anchor wheel F is rotatably mounted in the body frame E' (which is mounted in the body Z in a conventional manner) and carries an anchor F1 for the outer end of the spring G, the inner end which is secured to the spindle D by an end cap K and scale disc L. The inside end of spring H is fixed to the other end of spindle D by a similar end cap and scale disc. The outer end of spring H is anchored to a protrusion P on arm A. That arm carries two further protrusions Q and R, each bearing an indicating line which registers against a scale disc. Suppose the springs arm identical but are series mounted:

If now the applanating member is restrained by an external force applied at the applanating surface, preventing it from circular motion about the spindle, and the anchor wheel F is rotated through an angle of rotation O, the spindle will rotate through an angle of rotation O/2, because the spring rates are equal and the angular movement of the spindle is therefore half the total angular movement of the two series-mounted springs. The spindle rotates, and with it the scale discs, the scales of which register the force applied to the arm carrying the indicator lines. One or two windows S in the body Z of the tonometer allow the scales to be viewed.

At some convenient position, for example at one third of the travel of the arm from its forward urged position, the scale may be calibrated exactly and a fiduciary line engraved on the casing at T to indicate that position of calibration. However, if the restraining force is removed from the applanating member, which then rotates through an angle $d\theta$, it will cause the indicator lines to move through the same angle $d\theta$, while the discs will move in the same sense through $d\theta/2^1$ the angular ratio appropriate to the scales on the discs, and the indicators will always measure the force in the springs within their relative linearity limits.

If the rates of the two springs are not quite equal, then the rotation of the spindle will be a function of their rates. The advantages of the arrangement are that it permits a lower rate of spring to be used without binding coil on coil due to radial or tangential forces, and that adjustment is simply achieved. Furthermore, because the spindle is mounted in bearings in the rotating parts, it tends to rotate in the same direction as the force applied, thus minimizing the effect of friction.

The anchor wheel F derives its rotation from a coaxially mounted pinion U connected to anchor wheel F which co-operates with a gear wheel W actuated by the thumb of the operator. A co-operating rotary cam X on wheel W serves to operate a microswitch Y controlling the illumination for the applanating body. The construction allows for illumination of the applanated area by an illuminated ring or a plurality of illuminants directed towards the region of observation.

In an alternative arrangement, illustrated in FIG. 5, the scale discs may be omitted and a scale or scales 4 may be mounted coaxially with the thumb wheel W and the indicating line T is carried on the body Z of the tonometer. In that arrangement, the advantage of permanent indication veracity is lost, but the advantage of reduced change in force throughout the travel of the applanating body is retained. The position of disc L for the embodiment of FIGS. 1 to 4 is illustrated in FIG. 5 in broken line. Another modification made in the arrangement of FIG. 5 is to place the wheel W on the outside of the frame member E' instead of on the inside.

I claim:

1. An applanating tonometer having a body; an arm; and applanating member mounted on said arm; a spindle pivotally mounted with respect to said body, said arm being rotatably mounted on the spindle; two spiral springs; a manual adjustment knob rotatably mounted with respect to the body, said first spring being coupled at one end to said knob for being stressed upon rotation of said knob and being coupled at he other end to said spindle for urging said spindle to rotate when stressed by rotation of said knob and said second spiral spring being coupled at one end to said spindle for being stress when spindle is rotated and being coupled at the other end to said arm for urging said arm to rotate when stressed by rotation of said spindle; and indicator means coupled with said spindle for indicating the force applied to said arm through said springs, said springs extending in a direction for, when manual movement of said adjustment knob is effected, said first spring is stressed and thereby rotates said spindle, and said rotation of the spindle stressing said second spring and thereby rotating said arm about said spindle.

2. An applanating tonometer as claimed in claim 1 in which said indicator means comprises a graduated scale on said spindle an indicating line on said arm adjacent said scale so that the position of the arm can be read with respect to the spindle and a fiduciary mark on the body adjacent said arm to allow the arm to be aligned therewith to a calibrating position.

3. An applanating tonometer as claimed in claim 1 wherein said indicator means comprises a member coupled with said knob and carrying calibration markings on said member and a fiduciary mark on the body adjacent the portion of said member having said markings thereon whereby the position of the member and thus the knob may be read, thus giving an indication of the force applied to the spindle by virtue of the coupling of the knob to the spindle through said first spring.

* * * * *